United States Patent [19]

Gerarde, deceased et al.

[11] 4,003,262
[45] Jan. 18, 1977

[54] APPARATUS FOR MEASURING PRECISE MICRO QUANTITIES OF FLUID SAMPLES

[75] Inventors: Horace W. Gerarde, deceased, late of Tenafly, N.J.; by The Midlantic National Bank Citizens, executor, Englewood, N.J.

[73] Assignee: Becton, Dickinson and Company, East Rutherford, N.J.

[22] Filed: Dec. 16, 1974

[21] Appl. No.: 532,820

[52] U.S. Cl. .............................. 73/425; 128/DIG. 5
[51] Int. Cl.² .......................................... G01N 1/10
[58] Field of Search ............... 73/425.4 R, 425.4 P, 73/425.6; 23/230 B, 230 R; 128/DIG. 5

[56] References Cited

UNITED STATES PATENTS

| | | | |
|---|---|---|---|
| 3,433,712 | 3/1969 | Gerarde | 23/230 B |
| 3,518,804 | 7/1970 | Gerarde | 73/425.4 R |
| 3,779,083 | 12/1973 | Ayres | 73/425.4 P |

FOREIGN PATENTS OR APPLICATIONS 1,036,000  7/1966  United Kingdom ......... 128/DIG. 5

Primary Examiner—S. Clement Swisher
Assistant Examiner—Denis E. Corr
Attorney, Agent, or Firm—Kane, Dalsimer, Kane, Sullivan and Kurucz

[57] ABSTRACT

An apparatus for measuring precise micro quantities of fluid samples is disclosed which uses a precision, disposable, self-filling capillary tube on which a holder is mounted between its ends. A plastic adaptor is mounted on one of the ends so that when a protective shield is mounted on the holder the plastic adaptor makes sealing contact with the inner surfaces of the shield. The portion of the shield extending above the adaptor forms an overflow chamber which is utilized for mixing the fluid with a diluent. A vent is provided in the closed end of the shield so that the capillary tube is open to atmospheric pressure to permit the tube to fill with the sample while the shield is mounted in place on the holder.

3 Claims, 7 Drawing Figures

Fig. 6
Fig. 7
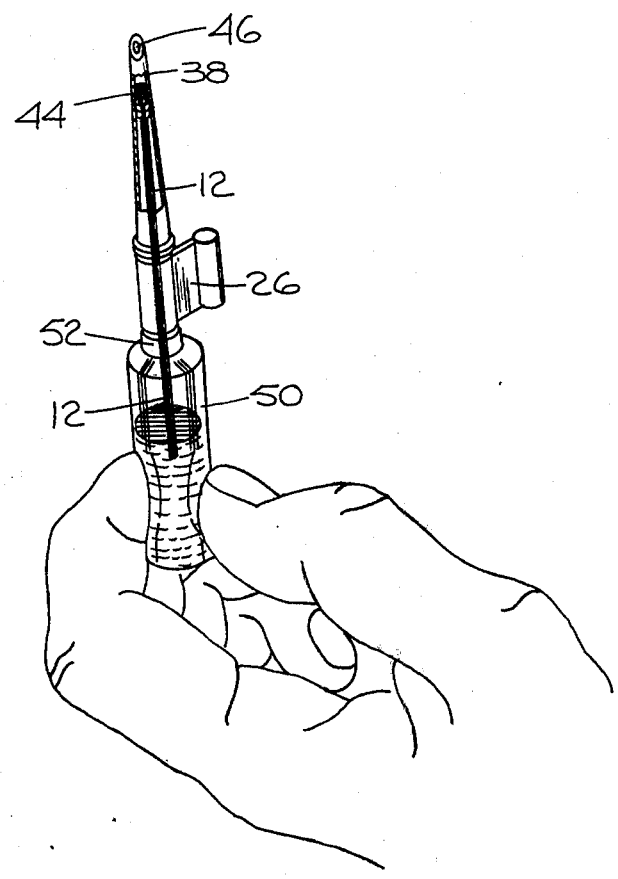
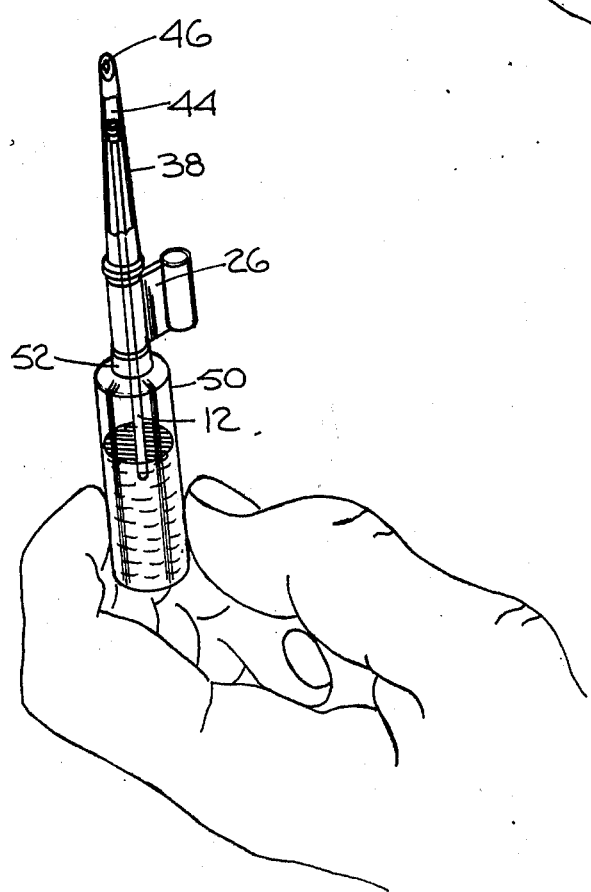

APPARATUS FOR MEASURING PRECISE MICRO QUANTITIES OF FLUID SAMPLES

BACKGROUND OF THE INVENTION

It is known to employ apparatus which utilizes a capillary tube of predetermined length mounted on a holder for collecting a predetermined accurately measured volume of fluid sample, for example plasma, serum or blood for subsequent testing as shown in U.S. Pat. No. 3,045,494. It is also known to employ capillary tubes for measuring capillary quantities of blood, for example up to 100 or more microliters. However, assemblies do not provide means for filling the tube and for flushing it into a diluent to remove all of the sample from the tube without losing any portion thereof — see for example U.S. Pat. No. 3,475,127.

It is important to obtain quantities of samples for blood testing which require volumes of more than 30, 40 or 50 microliters. However, when using capillary tubes of volumes greater than 50 microliters the tube becomes overly long, is fragile and readily breaks when handled. Samples for 100 microliters are generally obtained in microliter syringes which accurately measure the required volume. However, no means is provided for flushing the sample from the syringe so that all of the sample is discharged into a desired volume of diluent.

SUMMARY OF THE INVENTION

It is an object of the present invention to provide an apparatus for measuring precise micro quantities of fluid samples in which volumes of 100 microliters are obtainable without undue risk of breaking the assembly before use.

It is also an object of this invention to provide an apparatus which is adapted for coupling to a disposable, resilient container for discharging a desired volume of sample such as blood, plasma or serum collected in the capillary tube which provides means for flushing the capillary tube without loss of sample.

It is a further object of the invention to provide an assembly which is inexpensive to manufacture, which does not require skilled technicians to employ and which automatically and accurately measures a precise volume of sample to be tested without any loss of sample occurring during the transfer.

My invention generally contemplates the provision of an apparatus of collecting a precise volume of fluid such as blood or its component phases, plasma or serum, which is to be tested and in which the volume of sample is greater than 50 microliters.

The assembly includes a precision, disposable, self-filling capillary tube on which a holder is mounted between its ends. A plastic adaptor is mounted on one of the ends so that when a protective shield is mounted on the holder the plastic adaptor makes sealing contact with the inner surfaces of the shield so that the portion of the shield extending above the adaptor forms an overflow chamber which is utilized for mixing the fluid with a diluent. A vent is formed in the shield at its closed end and the capillary tube is open to atmospheric pressure to permit the tube to fill with the sample.

DESCRIPTION OF THE DRAWINGS

For a better understanding of the invention reference is had to the drawings which illustrate a preferred form of the invention herein.

FIGS. 2 through 7 are schematic representations of the steps utilized when employing the assembly of the invention herein.

DESCRIPTION OF THE PREFERRED EMBODIMENT

Figure 1:
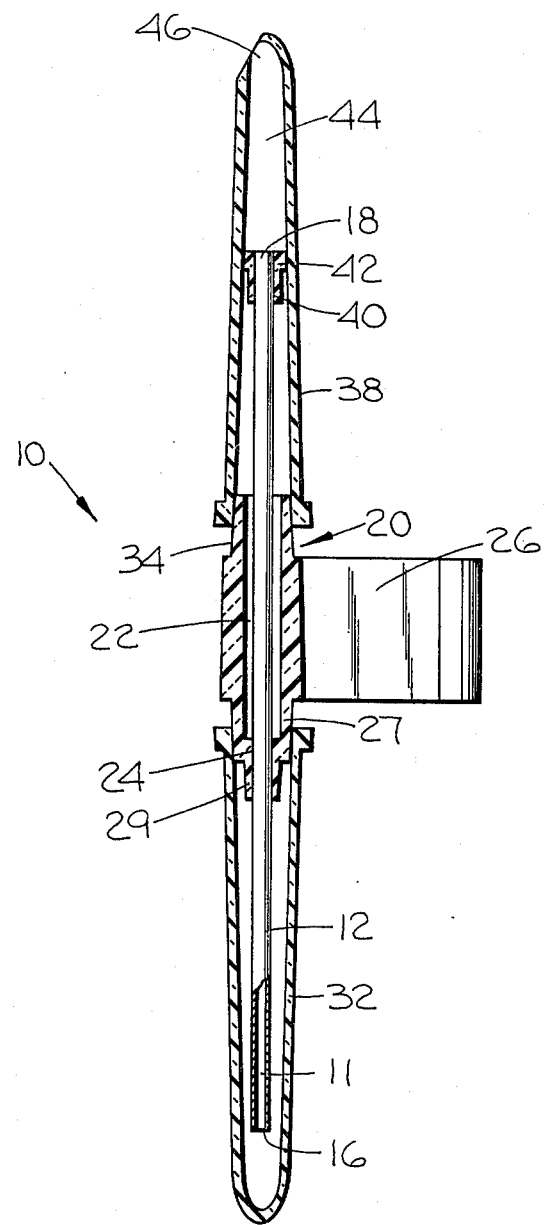
FIG. 1 is a sectional, elevational view of the apparatus fully assembled prior to use.

A better understanding of the invention will be had by referring principally to FIG. 1 which illustrates the component parts of the assembly.

The assembly 10 comprises a capillary tube 12 and a holder 20. Holder 20 is mounted between ends 16 and 18 of capillary tube 12. Holder 20 is formed having a bore 22 extending longitudinally therethrough having at one end thereof a section of reduced diameter 24 for mounting the capillary tube 12 in fixed position. Reduced bore section 24 is formed having a diameter which provides an interference fit relative to capillary tube 12. Also, holder 20 may have a similar reduced diameter bore at its other end to provide an interference fit if so desired.

Holder 20 is provided with finger engaging surfaces 26 which extend parallel to the longitudinal axis thereof and terminate between the ends of holder 20. The forward end of holder 20 forms a tapered tip or hub portion 27. Tapered tip 17 and reduced tapered tip 29 form the reduced diameter bore portion 24 of longitudinally extending bore 22.

Figure 2:
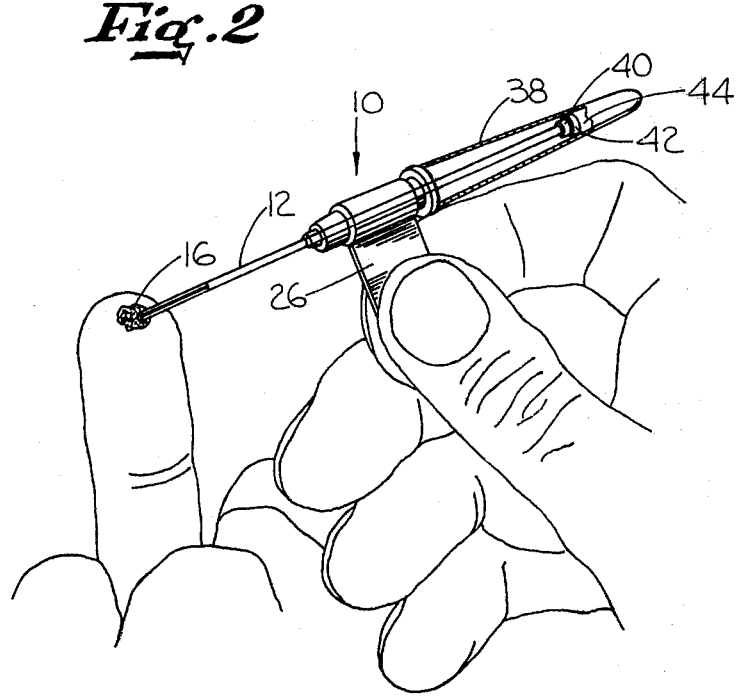

Shield 32 extends over the forward end of capillary 12 and is removably mounted on tapered tip or hub portion 27 of holder 20. Mounted at end 18 of capillary 12 is plastic adaptor 40 which is cylindrically formed and provides an interference fit on end 18 of capillary 12. The forward end of adaptor 40 is forced having a head or flanged portion 42 which extends radially from the longitudinal axis of capillary 12 so that flange 42 is adapted to form a sealing interference fit with the inner surfaces of shield 38 when mounted on holder 20 as illustrated in FIG. 1. Adaptor 40 engages the inner surfaces of shield 38 in a liquid tight seal so that the portion of shield 38 extending above adaptor 40 forms an overflow chamber 44. The closed end of shield 38 is formed having an opening 46 so that when the assembly is being used, as depicted in FIG. 2, the bore 11 of capillary tube 12 is open to atmosphere and thus will permit blood to flow into the capillary bore by capillary action.

Figure 3:
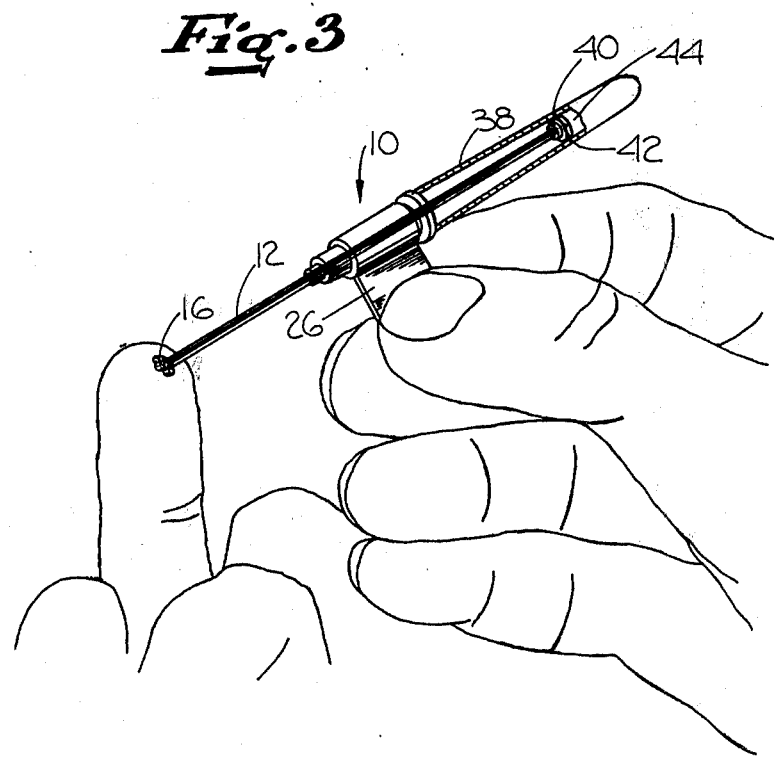
Figure 4:
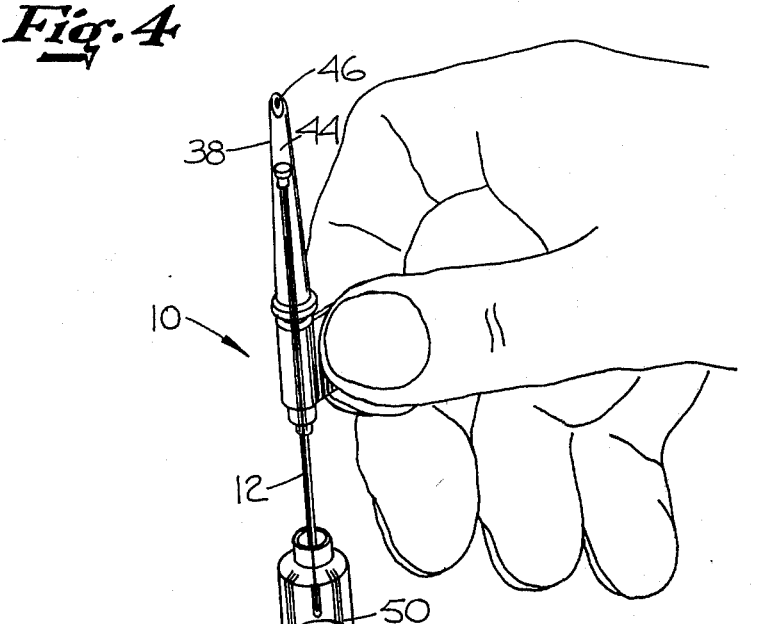
Figure 5:
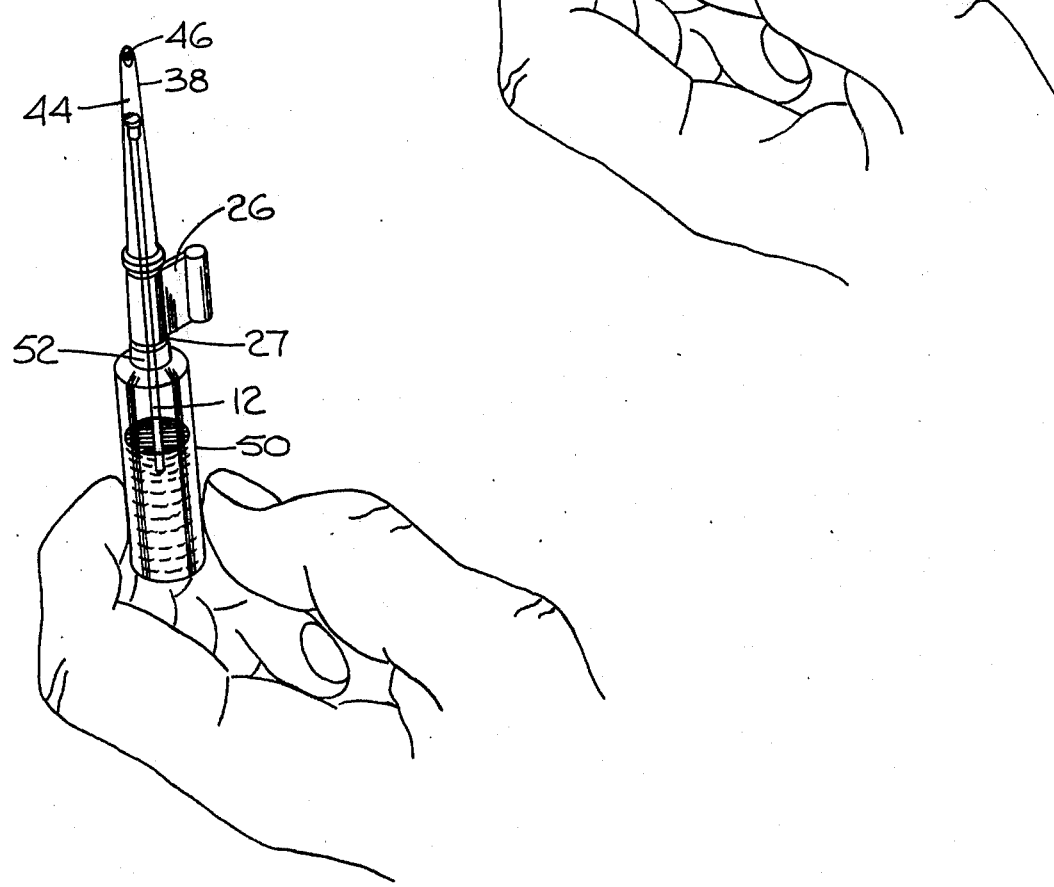

When utilizing the assembly as depicted in FIGS. 2 through 7 a digital puncture is made in the usual manner so that a drop of blood is formed at the forward end of a finger. Shield 32 is removed so that end 16 of capillary 12 is exposed and can be immersed in the drop of blood which will start to flow into bore 11 of capillary 12. In FIG. 3 capillary 12 is depicted as being completely filled with blood up to end 18 but not into overflow chamber 44. Thereafter, assembly 10 is removed from the drop of digital blood, the end is wiped clean and the exposed end 16 of capillary 12 is then inserted into a resilient container 50 containing an accurately measured volume of diluent as shown in FIG. 4. As assembly 10 is inserted into container 50 the container is compressed as illustrated in FIG. 4. When the assembly is mounted in the neck portion 52 of container 50 and contacts tapered end 27 in a sealing fit the pressure is released and the sample of blood is drawn into the diluent as illustrated in FIG. 5. Then, the bore 11 of capillary 12 is rinsed by squeezing resilient container 50 so that a mixture of sample and diluent flows through bore 11 and into overflow chamber 44. When bore 11 is completely rinsed, the compressive force on container 50 is removed and the mixture is again drawn back into the container as illustrated in FIG. 7. The rinsing of the bore can be accomplished in several repeated squeezing and releasing actions with container 50. Thus, all of the sample contained in bore 11 of capillary 12 is mixed uniformly with the diluent in container 50.

While variations of the invention herein may be had, the objectives of the invention have been illustrated and described. It is contemplated that changes in design can be made without departing from the spirit of the invention described herein.

What is claimed is:

1. An apparatus for measuring and diluting precise quantities of fluid samples comprising:
   a precision, self-filling capillary tube having the capability of holding a volume greater than 50 microliters;
   a holder having a longitudinally extending bore therethrough, said capillary being mounted in said bore and disposed so that said holder is positioned between the ends of the capillary, said bore providing an interference fit for holding the capillary tube in fixed position in said holder;
   a shield removably mounted on the holder and telescopically positioned over one end portion of said capillary tube;
   an adaptor mounted on said one end of said capillary tube and having surfaces thereon for making sealing contact with the inner surface of said shield so that the portion of said shield extending above said adaptor forms an overflow chamber;
   said shield having a vent formed in the closed end thereof so that the capillary tube is open to atmospheric pressure to permit said fluid samples to fill said tube by capillary action.

2. The apparatus of claim 1 wherein said adaptor is formed of a plastic material and said surfaces adapted to engage said shield capable of being deformed to form a liquid tight seal between said adaptor and said inner surfaces of said shield.

3. The apparatus of claim 1 wherein a second shield is removably mounted over the other end of said capillary to prevent contamination and breakage of the assembly prior to use.

* * * * *